(12) United States Patent
Joseph et al.

(10) Patent No.: US 9,607,266 B2
(45) Date of Patent: Mar. 28, 2017

(54) SYSTEMS AND METHODS FOR SIGNAL DETECTION IN PHARMACOVIGILANCE USING DISTRIBUTED PROCESSING, ANALYSIS AND REPRESENTING OF THE SIGNALS IN MULTIPLE FORMS

(71) Applicant: TATA CONSULTANCY SERVICES LIMITED, Mumbai (IN)

(72) Inventors: Archana Joseph, Kochi (IN); Bhushan Vidyadhar Bandekar, Mumbai (IN); Utsav Paragbhai Shah, Mumbai (IN); Jayant Sudhakarrao Dani, Mumbai (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 384 days.

(21) Appl. No.: 14/273,209

(22) Filed: May 8, 2014

(65) Prior Publication Data
US 2015/0032679 A1   Jan. 29, 2015

(30) Foreign Application Priority Data
Jul. 23, 2013   (IN) .......................... 2451/MUM/2013

(51) Int. Cl.
*G06N 5/04*   (2006.01)
*G06F 19/00*   (2011.01)

(52) U.S. Cl.
CPC ............. *G06N 5/04* (2013.01); *G06F 19/345* (2013.01)

(58) Field of Classification Search
None
See application file for complete search history.

(56) References Cited

U.S. PATENT DOCUMENTS

| | | | |
|---|---|---|---|
| 7,650,262 B2 | 1/2010 | Pearson et al. | |
| 2006/0288268 A1* | 12/2006 | Srinivasan | G06F 17/245 715/210 |
| 2007/0168334 A1* | 7/2007 | Julien | G06F 17/30595 |
| 2009/0076847 A1 | 3/2009 | Gogolak | |
| 2012/0143776 A1 | 6/2012 | Jaffe et al. | |
| 2013/0013332 A1 | 1/2013 | Frieder et al. | |

OTHER PUBLICATIONS

Lammel, Ralf. Google's MapReduce programming model—Revisited. Science of Computer Programming 70 (2008) 1-30.*

* cited by examiner

*Primary Examiner* — Stanley K Hill
*Assistant Examiner* — Robert H Bejcek, II
(74) *Attorney, Agent, or Firm* — Seed IP Law Group LLP

(57) ABSTRACT

Systems and methods for signal detection are described. The method comprises obtaining, by a data processing module, data from one or more data sources. The method further comprises standardizing the data, by the data processing module, based on at least one template to obtain standardized data. The standardized data have data properties depicting a format and a size of the data. Further, the method comprises determining, by an analysis module, one or more detection rules based on at least one of recommendation data and the data properties of the standardized data. The method further comprises detecting, by the analysis module, at least one signal present in the standardized data based on the one or more detection rules.

10 Claims, 2 Drawing Sheets

SYSTEMS AND METHODS FOR SIGNAL DETECTION IN PHARMACOVIGILANCE USING DISTRIBUTED PROCESSING, ANALYSIS AND REPRESENTING OF THE SIGNALS IN MULTIPLE FORMS

TECHNICAL FIELD

The present subject matter relates, in general, to signal detection, and particularly, but not exclusively, to, systems and methods for signal detection.

BACKGROUND

Signals may be defined as information-bearing patterns that convey information about behavior or attribute of some phenomenon and signal detection may be understood as a means to quantify the ability to distinguish between the signals and random energy patterns, such as noise that distract from the information. For example, in case of radar, dots on a screen of the radar confirm the presence of aircrafts. However, the dots may also appear on the screen due to some other object in the environment. In said example, presence of an aircraft may be understood as a signal and presence of the other objects may be understood as noise. In such a case, detection of a dot corresponding to the aircraft may be referred to as signal detection.

Further, various outcomes are possible during detection of the signal, such as a hit, a miss, a false alarm, and a correct rejection. In case of the hit, the dot corresponding to the aircraft is correctly identified. In case of the miss, it is wrongly identified that none of the dots correspond to the aircraft. In case of the false alarm, wrong dot is identified as the aircraft on the screen of the radar. In case of the correct rejection, dots corresponding to the other objects are correctly identified.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
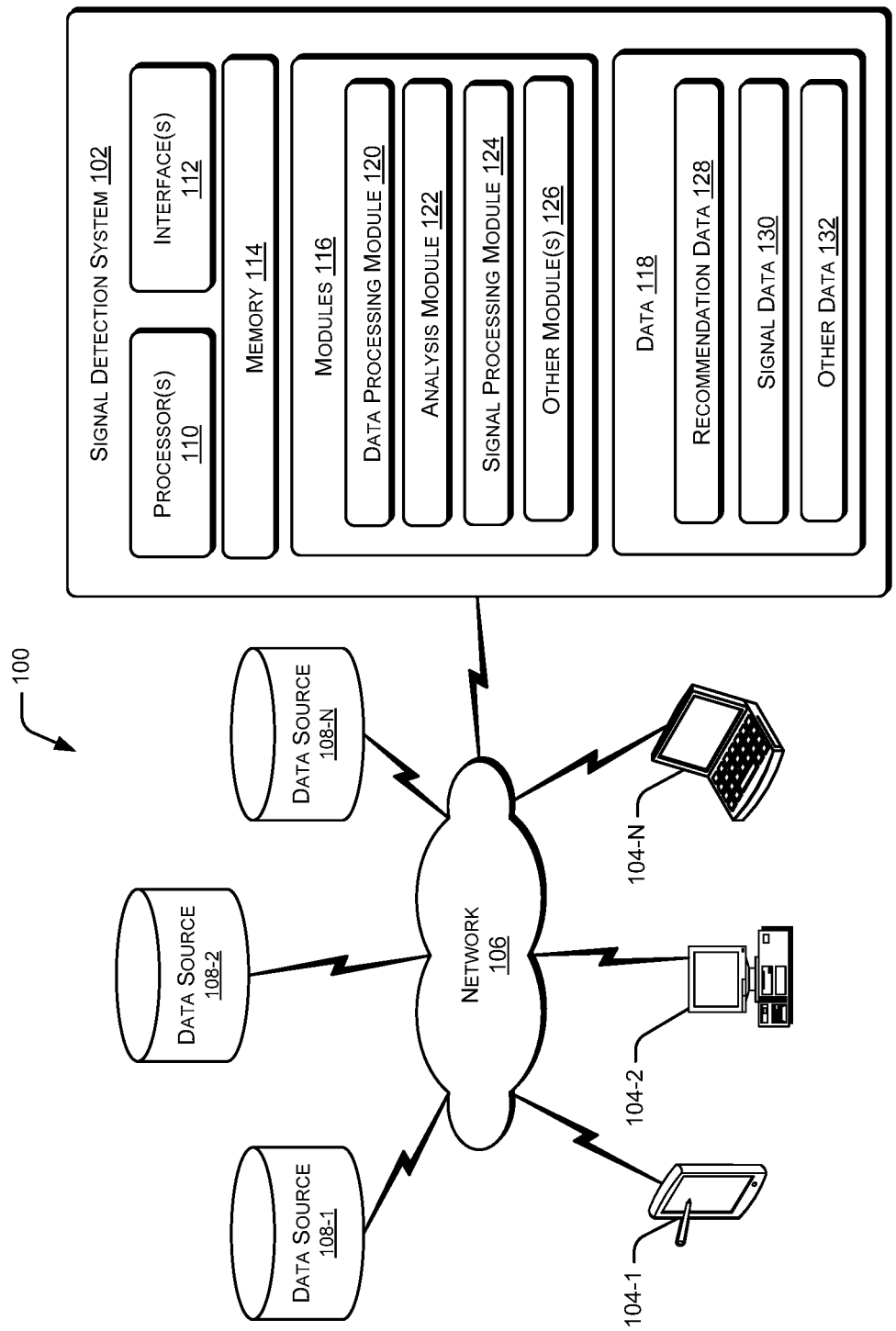
FIG. 1 illustrates a network environment implementing a signal detection system, in accordance with an embodiment of the present subject matter.

Nowadays various signal detection systems are available to detect presence of signals. A conventional signal detection system is generally specific to a particular type of signals and may not be able to detect any other signals other than it is designed for. For example, the conventional signal detection system, for detecting signals in pharmacovigilance data, may be applicable to field of pharmacovigilance only and may not be able to detect the signals present in other fields, such as networks and banking. Further, in case of the conventional detection system, it may not be feasible to add newly defined rules for signal detection. Furthermore, the conventional signal detection system may not allow a user to select a different statistical method other than the one for which the conventional signal detection system is designed for.

According to an embodiment of the present subject matter, systems and methods for signal detection are described herein. The systems and methods for signal detection are applicable to various fields having different types of data, such as pharmacovigilance data, call detail record data, network congestion data, bank transactional data, money laundering data, strength analysis data, calibration data, acoustic data, mining data, and social-media data. The systems and methods can be implemented in a variety of computing systems. Examples of such computing systems include, but are not restricted to, mainframe computers, workstations, personal computers, desktop computers, minicomputers, servers, multiprocessor systems, laptops, network servers, and the like.

In one implementation, initially, data is obtained from one or more data sources for determining the signals present in the data. The data may have any kind of information-bearing patterns, such as pharmacovigilance data, call detail record data, network congestion data, bank transactional data, money laundering data, strength analysis data, calibration data, acoustic data, mining data, and social-media data. The data generally include various hidden signals in it. These signals may indicate some relevant information about an event in a particular field. For example, network data of a network may have a signal present in it indicating network congestion at a particular node in the network. For example, the network data, such as delay in packets and packet loss may have the signal that a particular node is cause for network congestion. The data obtained from the one or more data sources may include structured data and unstructured data. Examples of the structured data may include, transactional data, records, files, and reports having text data and examples of the unstructured data may include audio, video, and images.

Further, the one or more data sources may include Comma-Separated Value (CSV) files, American Standard Code for Information exchange (ASCII) files, social media, social networking site, Statistical Analysis System (SAS), Open-Database Connectivity (ODBC), Attribute-Relation File Format (ARFF) files, binary files, Uniform Resource Locator (URL) files, Statistical Package for Social Science (SPSS), sequence files, stata, mail box files, and other data sources.

Since the data obtained from the one or more data source is of various types and is structured and unstructured, the data may be then standardized based on at least one template. In one implementation, the at least one template may be selected based on the type of the data to be standardized. In one implementation, the at least one template may be selected based on user recommendations or preferences. The template may include set of rules defined for standardizing the data. For example, the audio and video files may be converted into text files, so that the data is standardized. Thereafter, the template may be applied to the data using the map-reduce programming model for standardizing and simultaneously, making use of the distributed processing for standardizing. Further, once the standardization of the data is complete, standardized data is obtained for further processing. The standardization of the data is performed so that the data is uniform and consistent throughout and it can be analyzed without any complex computations.

Thereafter, one or more detection rules are determined based on at least one of recommendation data and data properties of the standardized data. In one implementation, based on the data properties of the standardized data, the one or more detection rules may be determined for detecting signals in the data. In another implementation, the one or more detection rules may be determined based on recommendations from the user. Further, in cases where recommendation from the user is considered in determination of the one or more detection rules, the recommendations from the user may be stored in the recommendation data for future purpose. The one or more rules may rely on various mechanisms, such as Bayes Propogation Neural Network (BCPNN), Gamma Poisson Shrinker (GPS), Multi Item Gamma Poisson Shrinkage (MGPS), Proportional reporting ratio (PRR), Urn-model based algorithm, Empirical Bayes Geometric Mean (EBGM), Information Component (IC), and Reporting Odds Ratio (ROR). In one implementation, these algorithms may be modified to identify the signals using distributed processing.

Further, the standardized data may be processed based on the one or more detection rules to detect at least one signal present in the data. In an example, primary signals may be identified and then, depending upon an iteration factor. Thereafter, the standardized data for which the signals have been identified may be removed. Subsequently, signals referred to as secondary signals may determined from the remaining standardized data. Similarly, tertiary signals and further, signals may be identified based on the iteration factor.

Once the signals are detected from the data, the signals may be stored in a distributed storage system. Thereafter, the signals stored in the distributed storage system may be processed to represent them in a plurality of forms, such as graphical visualization, top signals, cautioning reports, proactive data management reports, aggregated reports, and drill-down reports. Further, the processed signals in the plurality of forms may be provided to various devices and web pages.

In one implementation, when a new detection rule is discovered, the new detection rule is subsequently added to the existing one or more detection rules. In an example, the user may add the new detection rule through a variety of statistical components.

The present subject matter thus, provides the systems and the methods for signal detection. The present subject matter discloses a generic signal detection system that is applicable to various types of data, such as pharmacovigilance data, call detail record data, network congestion data, bank transactional data, money laundering data, strength analysis data, calibration data, acoustic data, mining data, and social-media data. Further, the present subject matter uses distributed processing and distributed storage while analyzing and processing the signals for efficient detection of the signals present in the data. Further, the systems and the methods are capable of recommending the detection rules and at the same time, may take recommendations from the user. Furthermore, new detection rules may be added to the existing detection rules which increase the flexibility of the present subject matter.

Figure 2:
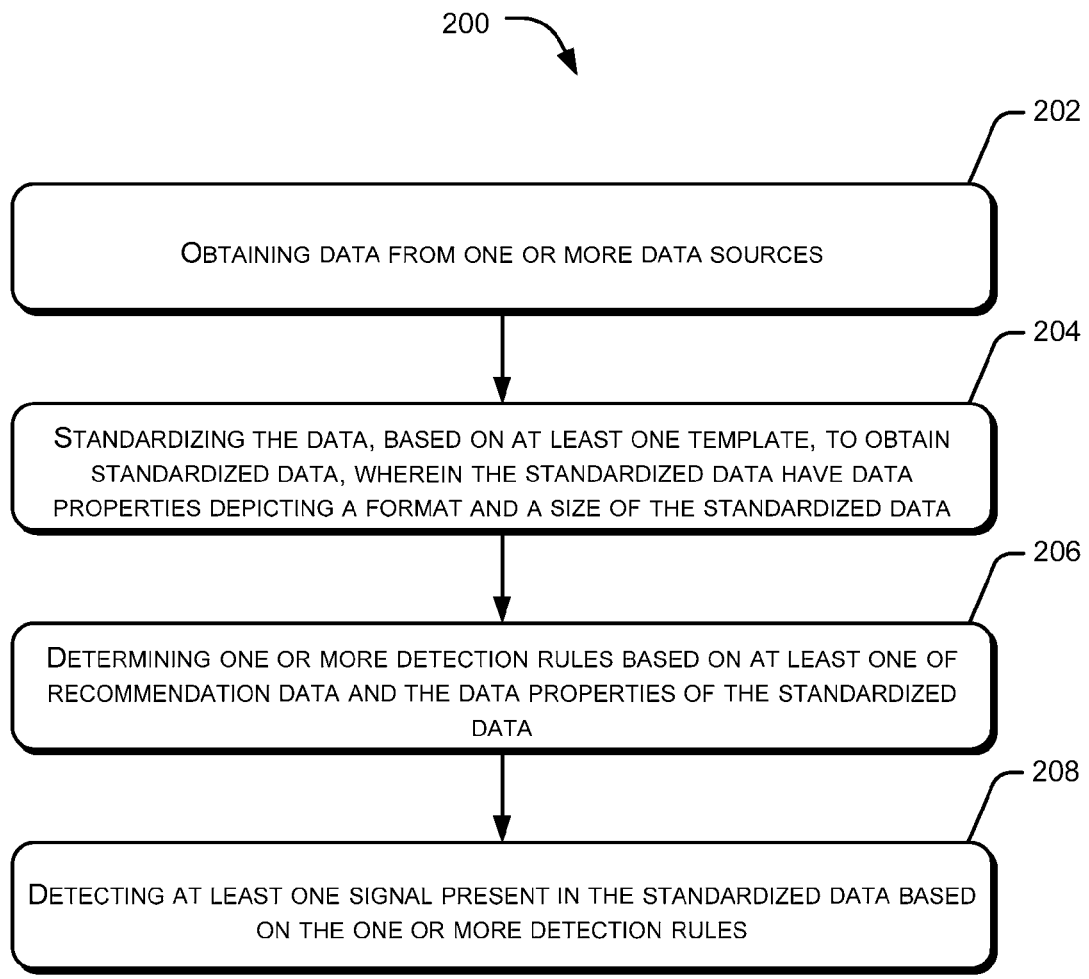
FIG. 2 illustrates a method for signal detection, in accordance with an embodiment of the present subject matter

The manner in which the systems and methods for signal detection shall be implemented is explained in detail with respect to FIGS. 1 to 2. While aspects of described systems and methods for signal detection may be implemented in any number of different computing systems, environments, and/or configurations, the embodiments are described in the context of the following system(s).

FIG. 1 illustrates a network environment 100 implementing a signal detection system 102 for signal detection, in accordance with an embodiment of the present subject matter. As shown in FIG. 1, the signal detection system 102, hereinafter referred to as a system 102, is communicatively coupled to user devices 104-1, 104-2, . . . , 104-N, through a network 106. For the sake of clarity, the user devices 104-1, 104-2, . . . , 104-N are collectively referred to as the user devices 104 and individually, referred to as the user device 104. Examples of the user devices 104 include, but are not restricted to, desktop computers, laptops, smart phones, personal digital assistants (PDAs), tablets, and the like. A user may use the user device 104 for providing his/her recommendations to the system 102. Further, the user may also use the user device 104 to see the signals detected by the system 102.

The user devices 104 are communicatively coupled to the system 102 over the network 106 through one or more communication links, for example, via dial-up modem connections, cable links, and Digital Subscriber Lines (DSL), wireless or satellite links, or any other suitable form of communication through the network 106. The network 106 may be a wireless network, a wired network or a combination thereof. The network 106 may be implemented as one of the different types of networks, such as intranet, Local Area Network (LAN), Wide Area Network (WAN), cloud based network, and the internet.

Further, as shown in FIG. 1, the system 102 is also communicatively coupled to one or more data sources 108-1, 108-2, . . . , 108-N, through the network 106. The one or more data sources 108-1, 108-2, . . . , 108-N are collectively, referred to as the data sources 108 and individually, referred to as the data source 108. In one implementation, the data source 108 may include various kind of data in different formats, such as Comma-Separated Value (CSV) files, American Standard Code for Information exchange (ASCII) files, social media, social networking site, Statistical Analysis System (SAS), Open-Database Connectivity (ODBC), Attribute-Relation File Format (ARFF) files, binary files, Uniform Resource Locator (URL) files, Statistical Package for Social Science (SPSS), sequence files, stata, and mail box files.

The system 102 may be implemented in a variety of computing devices, including, servers, workstations, computers, laptops, smart phones, personal digital assistants (PDAs), tablets, and the like.

In one implementation, the system 102 includes processor(s) 110, interface(s) 112, and a memory 114 coupled to the processor(s) 110. The interface(s) 112 may include a variety of application programs and hardware interfaces, for example, a network interface allowing the system 102 to interact with the user devices 104 and the data sources 108. The interface(s) 112 may also, facilitate multiple communications within a wide variety of networks and protocol types, including wired networks, for example, LAN, cable, etc., and wireless networks, such as WLAN, cellular, and satellite networks.

The processor(s) 110 may be implemented as one or more microprocessors, microcomputers, microcontrollers, digital signal processors, central processing units, state machines, logic circuitries, and/or any devices that manipulate signals based on operational instructions. Among other capabilities, the processor(s) 110 is configured to fetch and execute computer-readable instructions and data stored in the memory 114.

The memory 114 may include any non-transitory computer-readable medium known in the art including volatile memory, such as Static Random Access Memory (SRAM) and Dynamic Random Access Memory (DRAM), and/or non-volatile memory, such as Read Only Memory (ROM), erasable programmable ROM, flash memories, hard disks, optical disks, and magnetic tapes.

In one implementation, the system 102 may include module(s) 116 and data 118. The module(s) 116, amongst other things, include routines, programs, objects, components, data structures, etc., which perform particular tasks or implement data types. The module(s) 116 may also, be implemented as, signal processor(s), state machine(s), logic circuitries, and/or any other device or component that manipulate signals based on operational instructions.

Further, the module(s) 116 may be implemented in hardware, instructions executed by a processing unit, or by a combination thereof. The processing unit may comprise a computer, a processor, such as the processor(s) 110, a state machine, a logic array or any other suitable devices capable of processing instructions. The processing unit may be a general-purpose processor which executes instructions to cause the general-purpose processor to perform the required tasks or, the processing unit may be dedicated to perform the required functions.

In another aspect of the present subject matter, the module(s) 116 may be machine-readable instructions (software) which, when executed by a processor/processing unit, perform any of the described functionalities. The machine-readable instructions may be stored on an electronic memory device, hard disk, optical disk or other machine-readable storage medium or non-transitory medium. In one implementation, the machine-readable instructions may also be downloaded to the storage medium via a network connection.

In one implementation, the module(s) 116 further include a data processing module 120, an analysis module 122, a signal processing module 124, and other module(s) 126. The other module(s) 126 may include programs or coded instructions that supplement applications and functions of the system 102. The data 118 serves, amongst other things, as a repository for storing data processed, received, and generated by one or more of the other module(s) 126. The data 118 includes recommendation data 128, signal data 130, and other data 132. The other data 132 includes data generated as a result of the execution of one or more modules in the other module(s) 126.

In one embodiment of the present subject matter, the data processing module 120 may obtain data from one or more data sources 108 for determining signals present in the data. Examples of the data include, but are not limited to, pharmacovigilance data, call detail record data, network congestion data, bank transactional data, money laundering data, strength analysis data, calibration data, acoustic data, mining data, and social-media data.

Further, typically, the data may include structured data and unstructured data. In an example, the structured data comprises transactional data, records, files, and reports having text data and the unstructured data comprise audio, video, and images.

Thereafter, the data processing module 120 may standardize the data. In one implementation, the data processing module 120 may standardize the data based on at least one template. The at least one template may include set of rules for standardizing the data. In one example, in case of medicines, the at least one template may specify that a medicine may be considered by its chemical name rather than its proprietary name. In an implementation, the at least one template may specify that audio files should be converted to text files for the standardization of the data. In an example, the data processing module 120 may convert different types of data in different format to a common format, i.e., text files for standardization of the data.

In one implementation, the data processing module 120 may first determine whether any input from user is needed for standardization of the data or not. In case, the data processing module 120 identifies that the input is needed from the user, the data processing module 120 may obtain the at least one template from the recommendation data 128. In one example, the data processing module 120 may identify that the input is needed based on a user criteria. The user criteria may specify that whenever a particular format of data or data from a particular field is received, the data processing module 120 should take the input from the user. The recommendation data 128 may have recommendations for the user for selecting the at least one template. In one implementation, whenever the user selects a template for standardization, the preference or recommendation is stored in the recommendation data 128. Once the at least one template is selected based on the recommendation data 128, the data processing module 120 may apply the template to the data to obtain the standardized data. For example, different formats of the data may be converted to a common format so that the data is standardized. Further, the at least one template determined based on the recommendation data 128 may be stored for further usage so that the preferences or recommendations from the user may not be needed again and again, whenever same type of data is obtained for standardization.

On the other hand, in case the data processing module 120 identifies that recommendation from the user is not needed for selecting the at least one template, the data processing module 120 may select the at least one template based on data properties of the data. Subsequently, based on the at least template, the data processing module 120 may standardize the data to obtain the standardized data. Further, the data processing module 120 may assign a priority to each of the templates based on similarity of the templates to the data. For example, the templates having set of rules for converting the audio files to text files may have higher priority, in case the data comprises audio files. In case, where more than one template can be applied to the data for standardization, selection of the template may be done based on the priority assigned to the templates.

In one implementation, the data processing module 120 may apply the at least one template to the data using the map reduce programming model for standardizing the data by making use of the distributed processing. The map reduce programming model is typically used for processing large data sets with a parallel, distributed algorithm on a cluster.

Thereafter, the analysis module 122 may determine one or more detection rules based on at least one of the recommendation data 128 and the data properties of the standardized data. The data properties may include, length of the data, size of the data, and format of the data In one implementation, the one or more detection rules may rely on mechanisms based on Bayes Propogation Neural Network (BCPNN), Gamma Poisson Shrinker (GPS), Multi Item Gamma Poisson Shrinkage (MGPS), Proportional reporting ratio (PRR), Urn-model based algorithm, Empirical Bayes Geometric Mean (EBGM), Information Component (IC), and Reporting Odds Ratio (ROR).

In one implementation, the analysis module 122 may determine whether recommendation for determining the one or more detection rules in needed or not. In case, the analysis module 122 identifies that the recommendation is needed, the analysis module 122 may determine the one or more detection rules based on user recommendation. In an example, the user may input his/her preferences or recommendation to the system 102 through the user device 104. Thereafter, the recommendations for determining the one or more detection rule may be stored in the recommendation data 128. Whenever, recommendation is needed, the analysis module 122 may obtain the user recommendations from the recommendation data 128.

Further, in case the analysis module 122 identifies that the recommendation for determining the one or more detection rules is not needed, the analysis module 122 may determine the one or more detection rules based on the data properties of the standardized data.

Returning to the process of signal detection, in one implementation, when a new detection rule is discovered by the analysis module 122, the new detection rule is subsequently added to the existing one or more detection rules. In an example, the analysis module 122 may determine whether components needed for addition of the new detection rule is present in the system 102 or not. In an example, the components may be programming tools for creating the new detection rule. In case, the analysis module 122 determines that the components are not present in the system 102, the analysis module 122 may add the components and store the components for addition of the new detection rule. On the other hand, in case the components are already present in the system 102, the analysis module 122 may just select the components needed for addition of the new detection rule. Thereafter, upon obtaining the components, the analysis module 122 may define a flow for the new detection rule and the new detection rule is added to the system 102.

Once the one or more detection rules are determined, the analysis module 122 may detect at least one signal present in the standardized data based on the one or more detection rules. In one implementation, the analysis module 122 may follow an iterative approach for detection of the at least one signal in the data. For example, the analysis module 122 may process the standardized data and obtain signals referred to as primary signals. Thereafter, the analysis module 122 may remove the standardized data for which the primary signals have been identified. Subsequently, the analysis module 122 may detect signals from remaining standardized data left after removal of the standardized data for which the primary signals are identified. These signals are referred to as secondary signals. Similarly, the analysis module 122 may detect tertiary signals and further signals based on an iteration factor.

Further, an example is provided to illustrate detection of signals in case of pharmacovigilance data. In said example, the signal specifies casual relationship between drug and adverse event. Further, the numerical estimate of sensitivity is obtained by using the proportional reporting ratio algorithm. Table 1 has been provided below to provide the standardized sample data used in said example.

TABLE 1

| S No. | Adverse Event | Drug name | PRR |
| --- | --- | --- | --- |
| 1 | Cardiac disorder | ALPRAZOLAM | 0.39 |
| 2 | Cardiac disorder | ENALAPRIL MALEATE | 1.32 |
| 3 | Cardiac disorder | BISOPROLOL | 0.75 |
| 4 | Cardiac disorder | CADUET | 1.88 |
| 5 | Cardiac disorder | LASIX | 1.47 |

TABLE 1-continued

| S No. | Adverse Event | Drug name | PRR |
| --- | --- | --- | --- |
| 6 | Cardiac disorder | ZOCOR | 1.46 |
| 7 | Cardiac disorder | SYNAGIS | 2.48 |
| 8 | Cardiac disorder | RAMIPRIL | 1.03 |
| 9 | Cardiac disorder | CLONAZEPAM | 0.28 |
| 10 | Cardiac disorder | PROZAC | 1.01 |

Further, Table 2 depicts four possibilities in the signal detection. The four possibilities are: drug and adverse event, drug and other adverse event, other drugs and adverse event, and other drugs and other adverse events.

TABLE 2

| AE/Drug | Adverse Event (AE) | Other AE's |
| --- | --- | --- |
| Drug | a | b |
| Other drugs | c | d |

In said example, signal detection is performed when adverse event is Cardiac Disorder and drug name is PROPEFENONE. Further, a's count is 1, b's count is 1, c's count is 1205, and d's count is 354335. In one implementation, the analysis module 122 may calculate the PRR for signal detection based on equation 1.

$$PRR=[a/(a+b)]/[c/(c+d)] \quad \text{Equation 1}$$

After putting the values of a's count, b's count, c's count, and d's count in Equation 1, the PRR may be calculated.

$$PRR=[1*(1205+354335)]/[1205*(1+1)]$$

$$PRR=355540/2410=147.53$$

Further, the analysis module 122 may define a threshold for determining the presence of the signal. In said example, the threshold may be set to 100. As it is evident from the calculation that the PRR is much higher than the threshold, it may be identified as a signal. In this manner, the signal is detected in the data. Similarly, other numerical estimates of sensitivity may also be calculated.

In one implementation, once the at least one signal is detected from the data, the signal processing module 124 may store the at least one signal in a distributed storage system (not shown in FIG. 1). In one implementation, the signal processing module 124 may store the at least one signal in the signal data 130 present within the system 102. Thereafter, the signal processing module 124 may process the at least one signal to represent the at least one signal in a plurality of forms, such as graphical visualization, top signals, cautioning reports, proactive data management reports, aggregated reports, and drill-down reports. Further, the signal processing module 124 may provide the at least one of the signals in the plurality of forms to user devices 104 and various web pages. In one implementation, the signal processing module 124 may be configured to receive inputs from the user device 104, such as drill-down analysis related to detection of the signals.

Thus, the present subject matter provides a signal detection system 102 which is applicable for various types of data. Further, the present subject matter uses distributed processing and distributed storage while analyzing and processing the signals for efficient detection of the signals present in the data. Also, the systems and the methods are capable of recommending the detection rules and at the same time, may take recommendations from the user. Furthermore, new detection rules may be added to the existing detection rules which increase the flexibility of the present subject matter.

FIG. 2 illustrates method 200 for signal detection, in accordance with an embodiment of the present subject matter. The method 200 may be described in the general context of computer executable instructions. Generally, computer executable instructions may include routines, programs, objects, components, data structures, procedures, modules, functions, etc., that perform particular functions or implement particular abstract data types. The method 200 may also be practiced in a distributed computing environment where functions are performed by remote processing devices that are linked through a communications network. In a distributed computing environment, computer executable instructions may be located in both local and remote computer storage media, including memory storage devices. The method described herein, may be implemented by computer-executable instructions in one or more computer-readable media (for example, computer storage media or other tangible media). Further, the methods described herein, may be implemented in a plurality of programming languages.

The order in which the method 200 is described is not intended to be construed as a limitation, and any number of the described method blocks may be combined in any order to implement the methods, or alternative methods. Additionally, individual blocks may be deleted from the method 200 without departing from the spirit and scope of the subject matter described herein. Furthermore, the methods may be implemented in any suitable hardware, software, firmware, or combination thereof.

Referring to FIG. 2, a process for detecting a signal is disclosed. At block 202, data from one or more data sources 108 is obtained. Examples of the data include information-bearing patterns, but are not limited to, pharmacovigilance data, call detail record data, network congestion data, bank transactional data, money laundering data, strength analysis data, calibration data, acoustic data, mining data, and social-media data. In one implementation, the data processing module 120 may obtain the data from the one or more data sources 108. Further, the data may include structured data and unstructured data.

At block 204, the data is standardized based on at least one template to obtain standardized data. In one implementation, the data processing module 120 may standardize the data based on the at least one template. The at least one template may be defined as a set of rules defined for standardizing the data. In an example, the data processing module 120 may determine the at least one template based on user recommendation. In another example, the data processing module 120 may determine the at least one template based on data properties of the standardized data. The data properties of the standardized data may include a format and a size of the standardized data. In one implementation, the data processing module 120 may store the user recommendation in the recommendation data 128, so that whenever the same type of data is obtained for standardization, the data processing module 120 may determine the at least one template from the recommendation data 128. Further, in one implementation, the data processing module 120 may apply the at least one template to the standardized data using the map reduce programming model.

At block 206, one or more detection rules are determined based on at least one of the recommendation data 128 and data properties of the standardized data. In one implementation, the recommendation data (128) includes recommendations received from a user. The recommendations may indicate a user selection for a detection rule from amongst the one or more detection rules. In an example, the one or more detection rules may rely on various mechanisms, such as Bayes Propogation Neural Network (BCPNN), Gamma Poisson Shrinker (GPS), Multi Item Gamma Poisson Shrinkage (MGPS), Proportional reporting ratio (PRR), Urn-model based algorithm, Empirical Bayes Geometric Mean (EBGM), Information Component (IC), and Reporting Odds Ratio (ROR). In one implementation, the analysis module 122 may determine the one or more detection rules based on the user recommendations inputted by the user through the user device 104 or user recommendations stored in the recommendation data. In another implementation, the analysis module 122 may determine the one or more detection rules based on the data properties of the standardized data. Further, whenever a new detection rule is identified, the analysis module 122 may add the new detection rules to the system 102.

At block 208, at least one signal present in the standardized data is detected based on the one or more detection rules. In one implementation, the analysis module 122 may process the standardized data, based on the one or more detection rules, to detect the at least one signal present in the data. Further, the detected signals may be stored in the distributed storage system by the signal processing module 124. In one implementation, the signal processing module 124 may process the at least one signal stored in the distributed storage system to represent the at least one signal in a plurality of form. In an example, the plurality of forms may include graphical visualization, top signals, cautioning reports, proactive data management reports, aggregated reports, and drill-down reports. Furthermore, the signal processing module 124 may provide the at least one signal in plurality of forms to the user devices 104 and various web pages.

Although embodiments for signal detection have been described in the language specific to structural features and/or methods, it is to be understood that the invention is not necessarily limited to the specific features or methods described. Rather, the specific features and methods are disclosed as exemplary embodiments for signal detection.

We claim:
1. A signal detection system comprising:
   a processor;
   a data processing module executable by the processor to,
      obtain data from one or more data sources; and
      standardize the data, based on at least one template, to obtain standardized data, wherein the standardized data have data properties depicting a format and a size of the standardized data; and
   an analysis module executable by the processor to,
      determine one or more detection rules based on at least one of recommendation data and the data properties of the standardized data, wherein the recommendation data includes recommendations, received from a user, and wherein the recommendations indicate a user selection for a detection rule from amongst the one or more detection rules; and
      detect at least one signal present in the standardized data based on the one or more detection rules; and a signal processing module executable by the processor to:
- store the at least one signal in a distributed storage system; and
- process the at least one signal stored in the distributed storage system to represent the at least one signal in a plurality of forms, and wherein the plurality of forms includes graphical visualization, top signals, cautioning reports, proactive data management reports, aggregated reports, and drill-down reports.

2. The signal detection system as claimed in claim 1, wherein the at least one template is determined based on at least one of the recommendation data and the data properties of the standardized data.

3. The signal detection system as claimed in claim 1, wherein the at least one template is determined based on user recommendations stored in the recommendation data.

4. The signal detection system as claimed in claim 1, wherein the data processing module applies the at least one template to the standardized data using map reduce programming model for distributed processing.

5. The signal detection system as claimed in claim 1, wherein the analysis module executable by the processor further to identify a new detection rule and to add the new detection rule in the signal detection system.

6. A computer-implemented method for signal detection, the computer-implemented method comprising:
- obtaining, by a data processing module, data from one or more data sources;
- standardizing the data, by the data processing module, based on at least one template to obtain standardized data, wherein the standardized data have data properties depicting a format and a size of the standardized data;
- determining, by an analysis module, one or more detection rules based on at least one of recommendation data and the data properties of the standardized data, wherein the recommendation data includes recommendations, received from a user, and wherein the recommendations indicate a user selection for a detection rule from amongst the one or more detection rules;
- detecting, by the analysis module, at least one signal present in the standardized data based on the one or more detection rules; and
- storing, by a signal processing module, the at least one signal in a distributed storage system; and
- processing, by the signal processing module, the at least one signal stored in the distributed storage system to represent the at least one signal in a plurality of forms, and wherein the plurality of forms includes graphical visualization, top signals, cautioning reports, proactive data management reports, aggregated reports, and drill-down reports.

7. The computer-implemented method as claimed in claim 6, wherein the at least one template is determined based on at least one the recommendation data and the data properties of the standardized data.

8. The computer-implemented method as claimed in claim 6, wherein the standardizing comprises applying at least one template to the standardized data using map reduce programming model for distributed processing.

9. The computer-implemented method as claimed in claim 6, further comprises identifying a new detection rule and adding the new detection to a signal detection system.

10. A non-transitory computer readable medium having a set of computer readable instructions that, when executed, cause a computing system to:
- obtaining, by a data processing module, data from one or more data sources;
- standardizing the data, by the data processing module, based on at least one template to obtain standardized data, wherein the standardized data have data properties depicting a format and a size of the data;
- determining, by an analysis module, one or more detection rules based on at least one of recommendation data and the data properties of the standardized data, wherein the recommendation data includes recommendations, received from a user, and wherein the recommendations indicate a user selection for a detection rule from amongst the one or more detection rules;
- detecting, by the analysis module, at least one signal present in the standardized data based on the one or more detection rules;
- storing, by a signal processing module, the at least one signal in a distributed storage system; and
- processing, by the signal processing module, the at least one signal stored in the distributed storage system to represent the at least one signal in a plurality of forms, and wherein the plurality of forms includes graphical visualization, top signals, cautioning reports, proactive data management reports, aggregated reports, and drill-down reports.

\* \* \* \* \*